(12) United States Patent
Miles et al.

(10) Patent No.: US 8,840,641 B2
(45) Date of Patent: Sep. 23, 2014

(54) MEDICAL DEVICE FOR MODIFICATION OF LEFT ATRIAL APPENDAGE AND RELATED SYSTEMS AND METHODS

(75) Inventors: Scott D. Miles, Sandy, UT (US); Daryl R. Edmiston, Draper, UT (US)

(73) Assignee: Coherex Medical, Inc., Salt Lake City, UT (US)

( * ) Notice: Subject to any disclaimer, the term of this patent is extended or adjusted under 35 U.S.C. 154(b) by 71 days.

(21) Appl. No.: 12/684,795

(22) Filed: Jan. 8, 2010

(65) Prior Publication Data
US 2010/0228285 A1    Sep. 9, 2010

Related U.S. Application Data

(60) Provisional application No. 61/143,360, filed on Jan. 8, 2009, provisional application No. 61/160,247, filed on Mar. 13, 2009, provisional application No. 61/164,313, filed on Mar. 27, 2009.

(51) Int. Cl.
| | | |
|---|---|---|
| *A61B 17/00* | (2006.01) | |
| *A61B 17/12* | (2006.01) | |
| *A61B 17/04* | (2006.01) | |
| *A61B 17/122* | (2006.01) | |

(52) U.S. Cl.
CPC ....... *A61B 17/12022* (2013.01); *A61B 17/0401* (2013.01); *A61B 17/12159* (2013.01); *A61B 2017/00632* (2013.01); *A61B 2017/0437* (2013.01); *A61B 2017/0061* (2013.01); *A61B 17/0487* (2013.01); *A61B 2017/00592* (2013.01); *A61B 2017/00243* (2013.01); *A61B 17/122* (2013.01); *A61B 2017/00579* (2013.01); *A61B 2017/00575* (2013.01); *A61B 2017/0464* (2013.01); *A61B 2017/0448* (2013.01); *A61B 2017/0414* (2013.01); *A61B 2017/00588* (2013.01); *A61B 17/12172* (2013.01); *A61B 2017/00597* (2013.01); *A61B 17/12122* (2013.01); *A61B 2017/0446* (2013.01); *A61B 2017/0412* (2013.01); *A61B 2017/0409* (2013.01); *A61B 17/0057* (2013.01); *A61B 2017/00601* (2013.01); *A61B 2017/00867* (2013.01); *A61B 2017/0459* (2013.01)
USPC ........... 606/213; 606/200; 604/500; 604/506; 604/507; 604/508

(58) Field of Classification Search
None
See application file for complete search history.

(56) References Cited

U.S. PATENT DOCUMENTS

| | | | |
|---|---|---|---|
| 3,095,877 A | * | 7/1963 | Rowan ........................ 604/93.01 |
| 3,874,388 A | | 4/1975 | King et al. |

(Continued)

FOREIGN PATENT DOCUMENTS

| | | |
|---|---|---|
| DE | 10 2006 056 283 | 6/2008 |
| EP | 1 266 630 | 12/2002 |

(Continued)

OTHER PUBLICATIONS

International Search Report dated May 6, 2010, for International Application No. PCT/US2010/020539 (5 pages).

(Continued)

*Primary Examiner* — Melanie Tyson
*Assistant Examiner* — Todd J Scherbel
(74) *Attorney, Agent, or Firm* — Holland & Hart, LLP (57) ABSTRACT

Medical devices, systems and methods for modifying a left atrial appendage ("LAA"). In one embodiment, a medical device system includes a jailing member or structure positioned over the ostium of an LAA and at least one tissue growth member positioned within the LAA and retained within the LAA by the jailing member. In another embodiment, a medical device includes an atrial stent coupled with a patch that is configured to cover the ostium of an LAA. The patch may have a tissue growth member associated therewith. In another embodiment, the patch may include an open-cell frame which may be used as a jailing member or structure.

9 Claims, 6 Drawing Sheets

(56) References Cited

U.S. PATENT DOCUMENTS

| | | | |
|---|---|---|---|
| 5,192,301 A | 3/1993 | Kamiya et al. | |
| 5,284,488 A | 2/1994 | Sideris | |
| 5,334,217 A | 8/1994 | Das | |
| 5,425,733 A | 6/1995 | Schmieding | |
| 5,425,740 A | 6/1995 | Hutchinson | |
| 5,433,727 A | 7/1995 | Sideris | |
| 5,861,003 A | 1/1999 | Latson et al. | |
| 5,904,703 A | 5/1999 | Gilson | |
| 5,910,154 A | 6/1999 | Tsugita et al. | |
| 6,152,144 A * | 11/2000 | Lesh et al. | 128/898 |
| 6,174,322 B1 | 1/2001 | Schneidt | |
| 6,231,561 B1 | 5/2001 | Frazier et al. | |
| 6,238,403 B1 | 5/2001 | Greene et al. | |
| 6,290,674 B1 | 9/2001 | Roue et al. | |
| 6,328,727 B1 | 12/2001 | Frazier et al. | |
| 6,355,051 B1 | 3/2002 | Sisskind et al. | |
| 6,371,971 B1 | 4/2002 | Tsugita et al. | |
| 6,419,669 B1 | 7/2002 | Frazier et al. | |
| 6,436,088 B2 | 8/2002 | Frazier et al. | |
| 6,458,100 B2 | 10/2002 | Roue et al. | |
| 6,488,689 B1 | 12/2002 | Kaplan et al. | |
| 6,530,934 B1 * | 3/2003 | Jacobsen et al. | 606/157 |
| 6,551,303 B1 * | 4/2003 | Van Tassel et al. | 604/508 |
| 6,551,341 B2 | 4/2003 | Boylan et al. | |
| 6,561,969 B2 | 5/2003 | Frazier et al. | |
| 6,641,557 B1 | 11/2003 | Frazier et al. | |
| 6,650,923 B1 | 11/2003 | Lesh et al. | |
| 6,652,555 B1 | 11/2003 | VanTassel et al. | |
| 6,652,556 B1 | 11/2003 | VanTassel et al. | |
| 6,666,861 B1 | 12/2003 | Grabek | |
| 6,689,150 B1 * | 2/2004 | VanTassel et al. | 606/200 |
| 6,702,825 B2 | 3/2004 | Frazier et al. | |
| 6,706,065 B2 | 3/2004 | Langberg et al. | |
| 6,712,804 B2 | 3/2004 | Roue et al. | |
| 6,730,108 B2 | 5/2004 | Van Tassel et al. | |
| 6,746,472 B2 | 6/2004 | Frazier et al. | |
| 6,790,229 B1 | 9/2004 | Berreklouw | |
| 6,949,113 B2 | 9/2005 | Van Tassel et al. | |
| 6,979,344 B2 | 12/2005 | Jones et al. | |
| 6,994,092 B2 | 2/2006 | van der Burg et al. | |
| 7,011,671 B2 | 3/2006 | Welch | |
| 7,014,645 B2 * | 3/2006 | Greene et al. | 606/158 |
| 7,025,756 B2 | 4/2006 | Frazier et al. | |
| 7,044,134 B2 | 5/2006 | Khairkhahan et al. | |
| 7,056,294 B2 | 6/2006 | Khairkhahan et al. | |
| 7,115,110 B2 | 10/2006 | Frazier et al. | |
| 7,128,073 B1 | 10/2006 | van der Burg et al. | |
| 7,152,605 B2 | 12/2006 | Khairkhahan et al. | |
| 7,169,164 B2 | 1/2007 | Borillo et al. | |
| 7,192,439 B2 | 3/2007 | Khairkhahan et al. | |
| 7,226,458 B2 | 6/2007 | Kaplan et al. | |
| 7,293,562 B2 | 11/2007 | Malecki et al. | |
| 7,597,704 B2 | 10/2009 | Frazier et al. | |
| 7,608,091 B2 | 10/2009 | Goldfarb et al. | |
| 7,717,937 B2 | 5/2010 | Wahr et al. | |
| 7,727,189 B2 | 6/2010 | Van Tassel et al. | |
| 7,780,645 B2 * | 8/2010 | Jones | 604/507 |
| 7,842,054 B2 * | 11/2010 | Greene et al. | 606/158 |
| 8,142,470 B2 | 3/2012 | Quinn et al. | |
| 8,740,934 B2 | 6/2014 | McGuckin, Jr. | |
| 2001/0003161 A1 | 6/2001 | Vardi et al. | |
| 2002/0026094 A1 | 2/2002 | Roth | |
| 2002/0026217 A1 | 2/2002 | Baker et al. | |
| 2002/0062130 A1 | 5/2002 | Jugenheimer et al. | |
| 2002/0177855 A1 * | 11/2002 | Greene et al. | 606/108 |
| 2002/0183787 A1 | 12/2002 | Wahr et al. | |
| 2003/0014075 A1 | 1/2003 | Rosenbluth et al. | |
| 2003/0055455 A1 | 3/2003 | Yang et al. | |
| 2003/0057156 A1 | 3/2003 | Peterson et al. | |
| 2003/0120337 A1 | 6/2003 | Van Tassel et al. | |
| 2003/0125790 A1 | 7/2003 | Fastovsky et al. | |
| 2003/0171739 A1 * | 9/2003 | Murphy et al. | 606/1 |
| 2003/0181942 A1 | 9/2003 | Sutton et al. | |
| 2003/0187474 A1 | 10/2003 | Keegan et al. | |
| 2003/0191526 A1 | 10/2003 | Van Tassel et al. | |
| 2003/0195555 A1 | 10/2003 | Khairkhahan et al. | |
| 2003/0199923 A1 | 10/2003 | Khairkhahan et al. | |
| 2003/0204203 A1 | 10/2003 | Khairkhahan et al. | |
| 2003/0212432 A1 | 11/2003 | Khairkhahan et al. | |
| 2003/0220667 A1 | 11/2003 | van der Burg et al. | |
| 2004/0034366 A1 | 2/2004 | van der Burg et al. | |
| 2004/0122467 A1 * | 6/2004 | VanTassel et al. | 606/200 |
| 2004/0127935 A1 | 7/2004 | VanTassel et al. | |
| 2004/0215230 A1 | 10/2004 | Frazier et al. | |
| 2004/0260317 A1 | 12/2004 | Bloom et al. | |
| 2004/0267191 A1 | 12/2004 | Gifford, III et al. | |
| 2005/0004652 A1 | 1/2005 | van der Burg et al. | |
| 2005/0033409 A1 | 2/2005 | Burke et al. | |
| 2005/0043759 A1 | 2/2005 | Chanduszko | |
| 2005/0049573 A1 | 3/2005 | Van Tassel et al. | |
| 2005/0060017 A1 * | 3/2005 | Fischell et al. | 623/1.11 |
| 2005/0065589 A1 | 3/2005 | Schneider et al. | |
| 2005/0075665 A1 | 4/2005 | Brenzel et al. | |
| 2005/0090860 A1 | 4/2005 | Paprocki | |
| 2005/0113861 A1 * | 5/2005 | Corcoran et al. | 606/200 |
| 2005/0192616 A1 | 9/2005 | Callister et al. | |
| 2005/0192627 A1 | 9/2005 | Whisenant et al. | |
| 2005/0234540 A1 | 10/2005 | Peavey et al. | |
| 2005/0234543 A1 | 10/2005 | Glaser et al. | |
| 2005/0256532 A1 | 11/2005 | Nayak et al. | |
| 2005/0267524 A1 | 12/2005 | Chanduszko | |
| 2006/0009798 A1 | 1/2006 | Callister | |
| 2006/0009800 A1 | 1/2006 | Christianson et al. | |
| 2006/0036282 A1 | 2/2006 | Wahr et al. | |
| 2006/0052816 A1 | 3/2006 | Bates et al. | |
| 2006/0122646 A1 | 6/2006 | Corcoran et al. | |
| 2006/0149299 A1 * | 7/2006 | Greene et al. | 606/158 |
| 2006/0149307 A1 | 7/2006 | Durgin | |
| 2006/0149314 A1 | 7/2006 | Borillo et al. | |
| 2006/0206148 A1 | 9/2006 | Khairkhahan et al. | |
| 2006/0217761 A1 | 9/2006 | Opolski | |
| 2006/0276839 A1 | 12/2006 | McGuckin, Jr. | |
| 2007/0083230 A1 * | 4/2007 | Javois | 606/213 |
| 2007/0083232 A1 | 4/2007 | Lee | |
| 2007/0088388 A1 | 4/2007 | Opolski et al. | |
| 2007/0112382 A1 | 5/2007 | Thill et al. | |
| 2007/0123934 A1 | 5/2007 | Whisenant et al. | |
| 2007/0129757 A1 | 6/2007 | Armstrong | |
| 2007/0173885 A1 | 7/2007 | Cartier et al. | |
| 2007/0179527 A1 | 8/2007 | Eskuri et al. | |
| 2007/0179583 A1 | 8/2007 | Goetzinger et al. | |
| 2007/0191884 A1 | 8/2007 | Eskridge et al. | |
| 2007/0198059 A1 | 8/2007 | Patel et al. | |
| 2007/0237720 A1 | 10/2007 | Padilla et al. | |
| 2007/0276415 A1 | 11/2007 | Kladakis et al. | |
| 2008/0039929 A1 | 2/2008 | Davis et al. | |
| 2008/0119891 A1 | 5/2008 | Miles et al. | |
| 2008/0215086 A1 | 9/2008 | Olsen et al. | |
| 2009/0025820 A1 * | 1/2009 | Adams | 140/71 C |
| 2009/0069840 A1 | 3/2009 | Hallisey | |
| 2009/0099596 A1 * | 4/2009 | McGuckin et al. | 606/216 |
| 2009/0112249 A1 * | 4/2009 | Miles et al. | 606/192 |
| 2009/0318948 A1 * | 12/2009 | Linder et al. | 606/191 |
| 2010/0228279 A1 | 9/2010 | Miles et al. | |
| 2010/0234878 A1 | 9/2010 | Hruska et al. | |
| 2010/0324585 A1 | 12/2010 | Miles et al. | |
| 2010/0324586 A1 | 12/2010 | Miles et al. | |
| 2010/0324587 A1 | 12/2010 | Miles et al. | |
| 2010/0324588 A1 | 12/2010 | Miles et al. | |
| 2011/0022079 A1 | 1/2011 | Miles et al. | |
| 2011/0046658 A1 * | 2/2011 | Connor et al. | 606/200 |
| 2011/0054515 A1 | 3/2011 | Bridgeman et al. | |
| 2011/0208233 A1 * | 8/2011 | McGuckin et al. | 606/200 |
| 2012/0316584 A1 | 12/2012 | Miles et al. | |

FOREIGN PATENT DOCUMENTS

| | | |
|---|---|---|
| EP | 1 358 850 | 11/2003 |
| EP | 1 523 957 | 4/2005 |
| EP | 1 741 393 | 1/2007 |
| WO | 99/33402 | 7/1999 |
| WO | 00/27292 | 5/2000 |
| WO | 01/93920 | 12/2001 |
| WO | 02/071977 | 9/2002 |

(56) References Cited

FOREIGN PATENT DOCUMENTS

| WO | 03/028802 | 4/2003 |
|---|---|---|
| WO | 2004045393 A2 | 6/2004 |
| WO | 2005053547 | 6/2005 |
| WO | 2005099365 | 10/2005 |
| WO | 2006/033641 | 3/2006 |
| WO | 2006047748 A2 | 5/2006 |
| WO | 2007/054116 | 5/2007 |
| WO | 2007/147145 | 12/2007 |
| WO | 2010081033 A1 | 7/2010 |
| WO | 2010148246 A2 | 12/2010 |

OTHER PUBLICATIONS

International Search Report dated May 7, 2010, for International Application No. PCT/US2010/020547 (4 pages).

International Search Report dated Apr. 26, 2010, for International Application No. PCT/US2010/020549 (7 pages).

International Search Report dated Jun. 15, 2009, for International Application No. PCT/US2008/080374 (7 pages).

U.S. Appl. No. 12/684,783, filed Jan. 8, 2010, entitled "Medical Device for Modfication of Left Atrial Appendage and Related Systems and Methods."

U.S. Appl. No. 12/684,764, filed Jan. 8, 2010, entitled "Medical Device for Modfication of Left Atrial Appendage and Related Systems and Methods."

* cited by examiner

MEDICAL DEVICE FOR MODIFICATION OF LEFT ATRIAL APPENDAGE AND RELATED SYSTEMS AND METHODS

CROSS-REFERENCE TO RELATED APPLICATIONS

This application claims the benefit of U. S. Provisional Patent Application No. 61/143,360, filed Jan. 8, 2009, entitled MEDICAL DEVICE FOR MODIFICATION OF LEFT ATRIAL APPENDAGE AND RELATED SYSTEMS AND METHODS, and of U.S. Provisional Patent Application No. 61/160,247, filed Mar. 13, 2009, entitled MEDICAL DEVICE FOR MODIFICATION OF LEFT ATRIAL APPENDAGE AND RELATED SYSTEMS AND METHODS, and of U.S. Provisional Patent Application No. 61/164,313, filed Mar. 27, 2009, entitled MEDICAL DEVICE FOR MODIFICATION OF LEFT ATRIAL APPENDAGE AND RELATED SYSTEMS AND METHODS, the disclosure of each of which are incorporated by reference herein in their entireties.

TECHNICAL FIELD

The present invention relates generally to the modification of an atrial appendage and, more specifically, to devices, systems and methods for occluding or otherwise structurally altering such appendages.

BACKGROUND

The atrial appendage is a feature of all human hearts. The upper chambers of the heart, the atria, have this appendage attached to each of them. The physiologic function of such appendages is not completely understood, but they do act as a filling reservoir during the normal pumping of the heart. The appendages typically protrude from the atria and cover an external portion of the atria. Atrial appendages differ substantially from one to another in size, shape and specific location with respect to the atria. For example, one atrial appendage may be configured as a tapered protrusion while another atrial appendage may be configured as a re-entrant, sock-like hole. The inner surface of an appendage is conventionally trabeculated with cords of muscular cardiac tissue traversing its surface with one or more lobes.

The atrial appendages are inert while blood is being pumped through them during normal heart function. In other words, the appendages don't have a noticeable effect on blood pumped through them during normal heart function. However, in cases of atrial fibrillation, when the atria go into arrhythmia, blood may pool and thrombose inside of the appendages. Among other things, this can pose a stroke risk when it occurs in the left appendage since the thrombus may be pumped out of the heart and into the cranial circulation. Such can also lead to ischemic damage of other organs of the body.

Historically, atrial appendages have sometimes been modified surgically to reduce the risk imposed by atrial fibrillation. In more recent years, devices which may be delivered percutaneously into the left atrial appendage have been introduced. The basic function of these devices is to exclude the volume within the appendage with an implant which then allows blood within the appendage to safely thrombose and then to be gradually incorporated into cardiac tissue. This can leave a smooth, endothelialized surface where the appendage used to be.

In comparison to surgical procedures, devices implanted percutaneously are clearly a less invasive means for addressing the problems associated with the left atrial appendage. However, due to the wide variability of the size of the ostium and the volume of an atrial appendage, implant devices that are currently used typically include structure that cannot meet such variability, resulting in inadequate devices for many left atrial appendages. Further, such implant devices are substantially limited by the orientation by which they can successfully be deployed. Thus, successful placement and deployment of such devices becomes limited.

As such, it would be advantageous to provide percutaneous systems, methods and devices that, among other things, address one or more issues such as implant orientation and the variability in sizes of the left atrial appendage in order to provide high success in left atrial appendage modification.

BRIEF SUMMARY

The present invention includes embodiments directed to medical devices, medical device systems and methods for modifying an atrial appendage. In one embodiment, a medical device system is provided for modification of a left atrial appendage (LAA). The system includes a medical device having a framework including a jailing portion configured to be positioned against a sidewall of the left atrium of the heart and over an ostium of the LAA. A tissue growth member is configured to be retained within the LAA, wherein the tissue growth member is configured to be separate and discreet from the framework of the medical device. In one more particular embodiment, the medical device may be formed of a nickel-titanium alloy and the tissue growth member may include an expanding foam material. The tissue growth member may include a plurality of tissue growth elements that, in one embodiment, may be unconnected or, in another embodiment, may be tethered to one another.

In accordance with another embodiment, a medical device configured to modify a left atrial appendage is provided. The medical device includes a patch including a framework and a tissue growth member. The patch is sized and configured to extend against a sidewall of a left atrium to cover an ostium of the left atrial appendage. At least one looped structure extends from the patch and is configured to engage and bias against the sidewall of the left atrium of the heart. In one particular embodiment, the patch may include a plurality struts or frame segments defining one or more open cells such that the patch may function as a jailing member or structure. In another embodiment, a tissue growth member may be associated with the patch.

In accordance with another embodiment of the present invention, another medical device configured to modify a left atrial appendage is provided. The medical device includes a framework sized and configured to bias against the sidewall of the left atrium of the heart and over the ostium of a left atrial appendage. A tissue growth member is associated with at least a portion of the framework. The tissue growth member is sized and configured to cover the ostium of a left atrial appendage.

In accordance with a further embodiment of the present invention. a method of modifying a left atrial appendage is provided. The method includes positioning a jailing member over the ostium of a left atrial appendage. A catheter is inserted through an opening within the jailing member and at least one tissue growth member is disposed within the left atrial appendage. The at least one tissue growth member is retained within the left atrial appendage with the jailing member. In one embodiment, the medical device and tissue growth member may be delivered by the same catheter. In another embodiment, the medical device may be delivered by a first catheter and the tissue growth member may be delivered by a second catheter.

BRIEF DESCRIPTION OF THE SEVERAL VIEWS OF THE DRAWINGS

The foregoing and other advantages of various embodiments of the invention will become apparent upon reading the following detailed description and upon reference to the drawings in which.

DETAILED DESCRIPTION OF THE INVENTION

Figure 1:
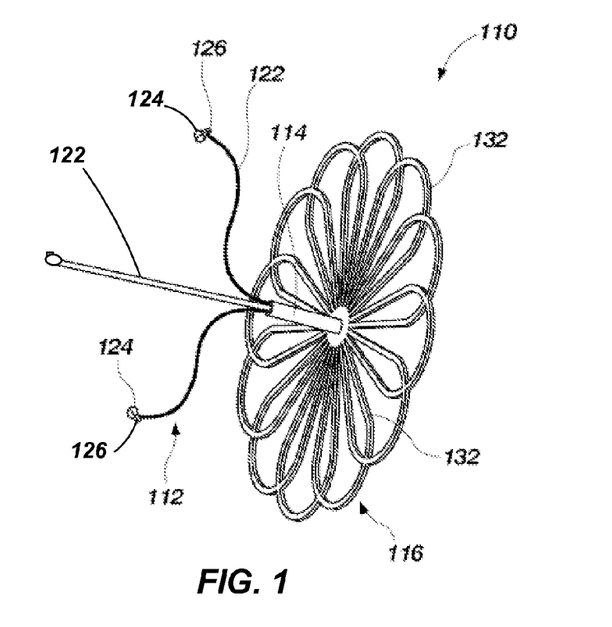
FIGS. 1 and 2 are respective perspective and side views of a medical device, according to an embodiment of the present invention.
Figure 2:
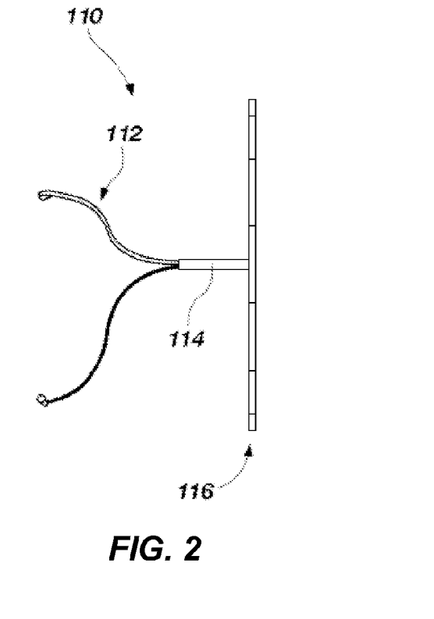
Figure 3:
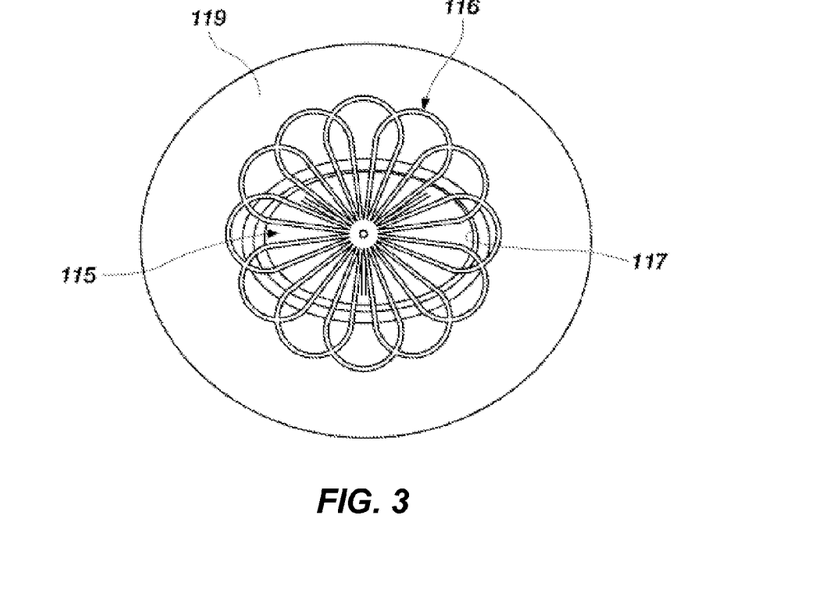
FIG. 3 is a front view of the medical device of FIGS. 1 and 2, depicting the medical device lodged within an atrial appendage, according to an embodiment of the present invention.

Referring to FIGS. 1 through 3, a medical device 110 for modifying an atrial appendage, such as a left atrial appendage (LAA). The medical device 110 includes a framework which may include an anchoring portion 112, an intermediate portion 114 and a jailing portion 116 (which may also be referred to as a restraining structure or caged portion). The medical device 110 is sized and configured to move between multiple configurations including a first, collapsed (or constrained) configuration and a second, expanded configuration. When moved to the collapsed configuration, the medical device 110 is collapsed within the narrow confines of a catheter. In the expanded configuration, the medical device is deployed from the catheter and self expands to be deployed relative to an atrial appendage.

The anchoring portion 112 may extend distally and radially outward from the intermediate portion 114. The individual anchors or legs of the anchoring portion 112 may include a curved portion 122 and a coiled portion 124. In the embodiment shown, the coiled portion 124 is located distal of the curved portion 122. The coiled portion 124 may also include tissue engagement members such as, for example, tapered nubs 126 located on an outer periphery of the coiled portion 124. With such an arrangement, the coiled portion 124 can engage and nest within the tissue of the LAA and the nubs 126 enable improved traction between the medical device 110 and the atrial appendage. The tapered nubs 126 may be configured to atraumatically engage the tissue of the LAA and, for example, nestle or engage the trabeculations within the LAA.

The intermediate portion 114 of the medical device 110 extends proximally of the anchoring portion 112 and is disposed intermediate or between the anchoring portion 112 and the jailing portion 116. The intermediate portion 114 may include a coiled structure or a spring that is sized and configured to provide a tensile biasing force between the anchoring portion 112 and the jailing portion 116 when deployed within an atrial appendage. The intermediate portion 114 may be interconnected with a central portion of the jailing portion 116 and extend distally of the jailing portion 116.

The jailing portion 116 may be configured with multiple struts or frame segments 132 that extend so as to define a substantially flat or planar structure when in a deployed state (e.g., FIG. 2). The intermediate portion 114 extends at an angle relative to the jailing portion 116 (or, stated another way, at an angle relative to a plane generally defined by the frame segments 132 of the jailing portion). For example, as shown in FIG. 2, the intermediate portion 114 may be substantially transverse or perpendicular to the jailing portion 116 when in the deployed state (i.e., as shown in FIGS. 1-3). The intermediate portion 114, the joint between the intermediate portion 114 and the jailing portion 116, or both, may be flexible so that the intermediate portion 114 may be oriented at a variety of angles relative to the jailing portion 116 when deployed within the atrial appendage. Such frame segments 132 of the jailing portion 116 may be interconnected so as to define a multi-cellular structure as seen in FIGS. 1 and 3. The jailing portion 116 is sized and configured to sit outside and over the ostium 117 of, for example, an LAA 115. With the anchoring position 112 engaged with the walls of an LAA 115, and the jailing portion abutting the side wall 119 of the left atrium and covering the ostium 117 of the LAA, the intermediate portion 114, which may include a spring or coil as described above, is configured to bias the jailing portion 116 against the side wall 119 of the left atrium.

Figure 4A:
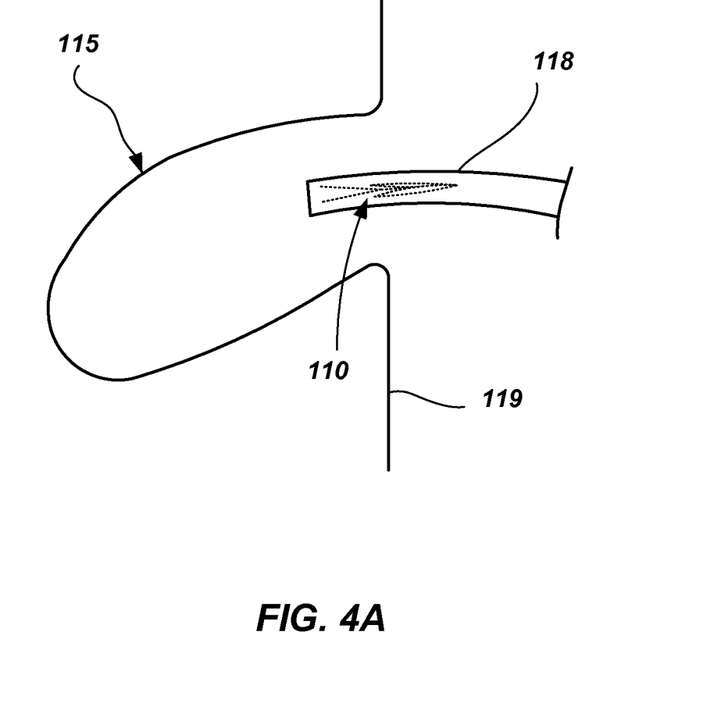
FIGS. 4A through 4E are side views of the medical device of FIGS. 1 and 2, depicting the medical device being deployed in an atrial appendage and depicting a tissue growth member being deployed and jailed within the atrial appendage.

With reference to FIGS. 4A through 4E, deployment or implantation of the medical device 110 at the LAA 115 along with a tissue growth member 140 is illustrated. Referring first to FIG. 4A, a catheter 118 is directed to the location of the LAA 115. Access to the LAA 115 may be obtained by, for example, advancing the catheter 118 through the right atrium and through the atrial septum wall of the heart via a transseptal puncture employing standard catheterization techniques as will be understood and appreciated by those of ordinary skill in the art. Imaging techniques, as known in the art, may be utilized for preferred positioning of the catheter 118 by advancing, for example, contrast through the catheter and into the left atrial appendage 115. It is noted that FIG. 4A shows the medical device 110 schematically in a constrained state within the catheter 118 during the advancing of the catheter 118 to the LAA 115.

Figure 4B:
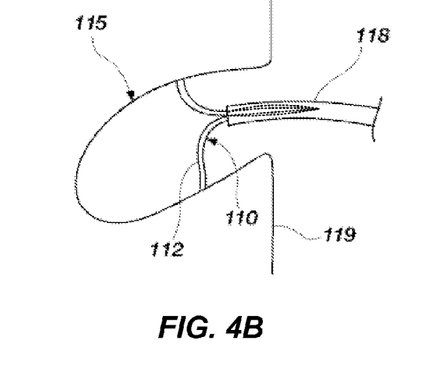
Figure 4C:
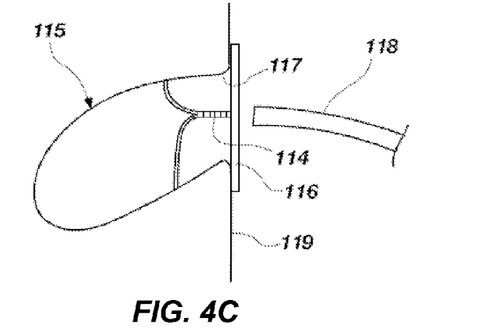

With the catheter 118 advanced within the LAA 115, the anchoring portion 112 of the medical device 110 may be deployed as shown in FIG. 4B. As previously set forth, the anchoring portion 112 is sized and configured to lodge within the LAA 115 and against the walls of the LAA 115. Once the anchoring portion 112 is lodged (i.e., engaged with the walls of the LAA 115), the catheter 118 can be moved proximally to deploy the intermediate portion 114 and the jailing portion 116 so that the jailing portion 116 is biased against the sidewall 119 of the left atrium and over the ostium 117 of the LAA 115, as depicted in FIG. 4C and as described above with respect to FIG. 3.

Figures 4D, 4E:
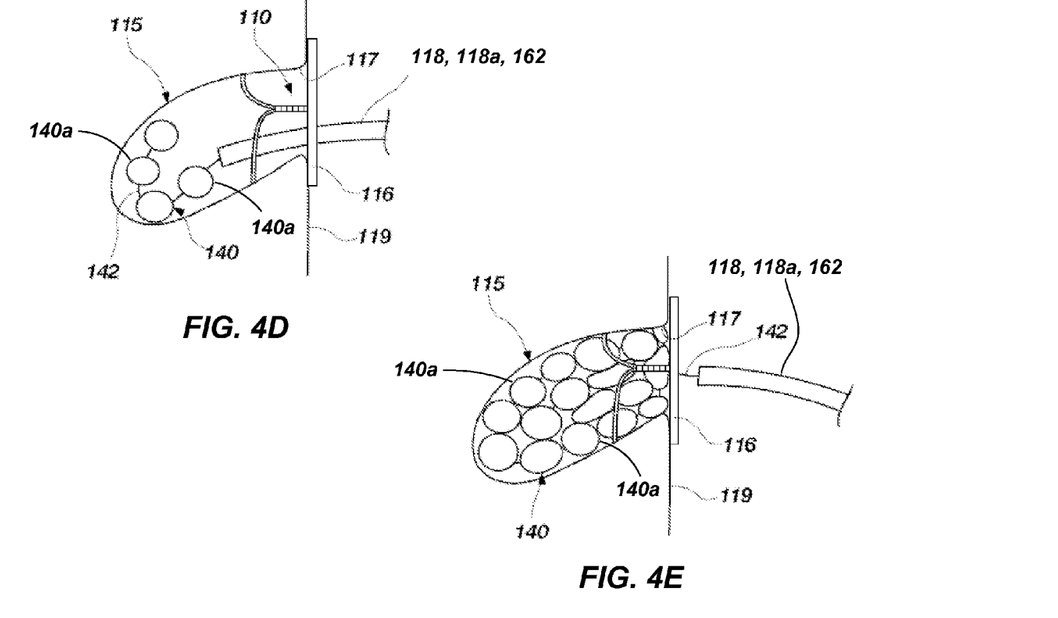

With reference to FIG. 4D and 4E, a catheter 118 (which may be the same catheter 118 that deployed the medical device 110 or a separate catheter 118a) may then be advanced through openings or cells defined by the frame segments 132 of the jailing portion 116 and into the LAA 115 to deploy one or more tissue growth members 140. In one embodiment, the tissue growth member 140 may include multiple tissue growth elements 140A interconnected by, for example, a tether 142. In another embodiment, the tissue growth member 140 may include a single tissue growth element or multiple tissue growth elements that are separate and unconnected from each other (i.e., without a tether or other connecting structure). Such deployment of tissue growth elements may be conducted in a manner similar to that described with respect to U.S. patent application Ser. No. 12/253,831, filed Oct. 17, 2008, entitled MEDICAL DEVICE FOR MODIFICATION OF LEFT ATRIAL APPENDAGE AND RELATED SYSTEMS AND METHODS, the disclosure of which is incorporated by reference herein. Additionally, such deployment may be conducted in a manner similar to that described with respect to U.S. patent application Ser. No. 12/428,360, filed Apr. 22, 2009, entitled DEVICE, SYSTEM AND METHOD FOR ANEURYSM EMBOLIZATION, the disclosure of which is incorporated by reference herein.

As depicted, once the volume of the LAA 115 is filled with the tissue growth member 140 so as to create a surface adjacent the ostium of the LAA 115 to substantially prevent thrombus from migrating from the LAA, the tether 142 (if utilized) may be released by snipping or cutting, and the catheter 118 may be withdrawn. In another embodiment, it is contemplated that the tether 142 may be formed as a continuous loop (or have its ends tied prior to being placed in the catheter 118, 118a) so that it is not necessary to cut the tether upon deployment. In the case that the tissue growth member 140 is a single tissue growth element or multiple, unconnected tissue growth elements (without a tether), the catheter 118 may simply be withdrawn once the physician is satisfied with the positioning of the tissue growth member.

The tissue growth member 140, once deployed from the catheter 118, self expands to a size that is larger than the openings or cells defined by the frame segments 132 of the jailing portion 116. Thus, once deployed, the tissue growth member 140 is jailed or retained within the LAA 115 and substantially prevented from migrating therefrom. Further, as a safety precaution, a tether 142 may further prevent the tissue growth member 140 from migrating from the LAA 115 in the case that, for example, one of the tissue growth elements 140a is able to migrate through the openings of the jailed portion 116. It is noted that the tether 142 may also be used in helping to recapture the tissue growth elements 140a within the catheter 118 in the case that a physician decides to reposition the tissue growth member or remove it completely for some reason.

According to one embodiment of the present invention, the tissue growth member 140 (or more particularly, the tissue growth elements 140a) may be self expanding porous members, such as a polymer based foam or a polyurethane foam. Other materials with desired porosity may also be used, such as, for example, felt, fabric, a polyester fiber such as polyethylene terephthalate (PET, also known commercially as Dacron®), Nitinol (a nickel-titanium alloy) braded wire, or Nitinol felt. In the case of foam, such foam may be a reticulated foam, typically undergoing a chemical or heating process to open the pours within the foam as known in the art. The foam may also be a non-reticulated foam. The tissue growth member 140 is configured to induce tissue in-growth therethrough to, thereby, close the LAA opening.

The tissue growth elements 140a may be formed as porous members that self expand, and may include, for example, a polymer based foam, a polyurethane foam, or any other material providing porosity to induce tissue in-growth. Further, the tether 142 of this embodiment may be formed from a polymer based material or any other suitable line suitable to facilitate interconnection between multiple tissue growth elements 140a. The framework of the medical device 110 may be formed from any biocompatible material, such as Nitinol, other shape memory alloys, or a polymeric material. In one embodiment, the framework of the medical device 110 may be laser cut, in whole or in part, from a flat sheet of Nitinol and may then be heat-set to a desired expanded shape.

Figure 5:
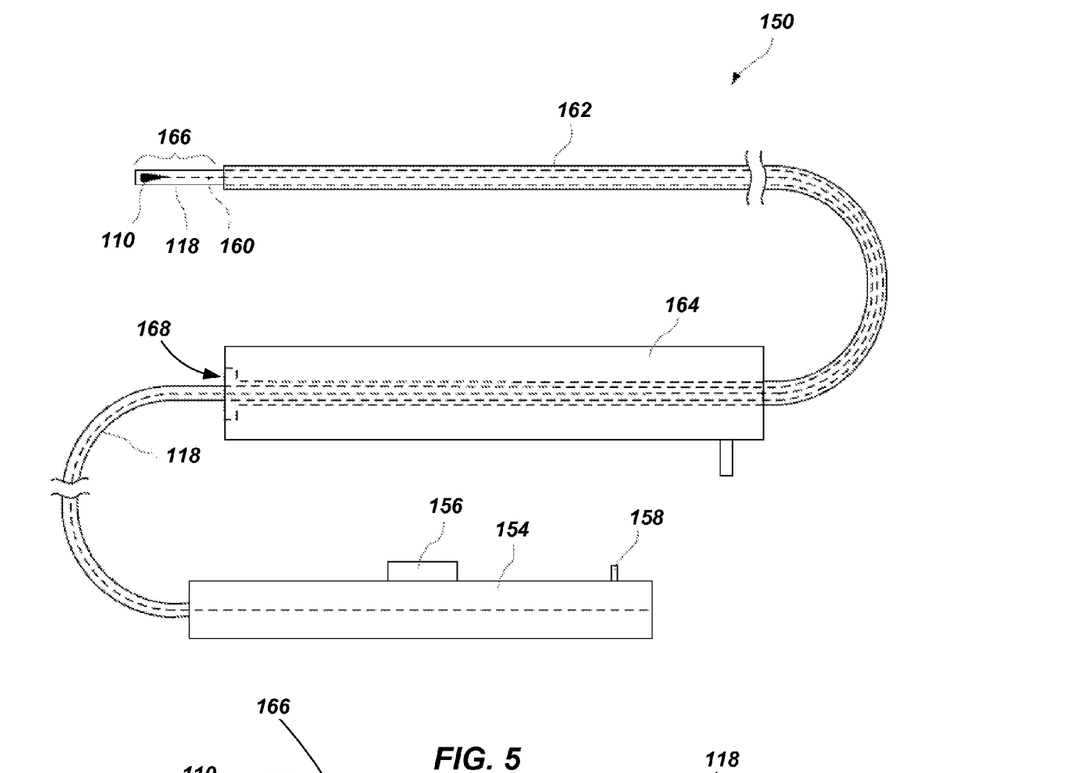
FIG. 5 is a schematic showing various components of a medical device system according to an embodiment of the present invention.

Referring briefly to FIG. 5, a medical device system 150 is shown which may be used for deployment of a medical device 110, the tissue growth members 140, or both. The medical device system 150 may include a device catheter 118 having handle 154 with an actuator 156 and fluid port 158. The device catheter 118 may also include a medical device 110 coupled with one or more tethers 160 disposed within the device catheter 118. The medical device system 150 may further include a primary catheter 162 with a handle 164 wherein the device catheter 118 is sized and configured to pass through a lumen of the primary catheter 162.

The medical device 110 may be positioned within a lumen of the device catheter 118 at a distal portion 166 thereof. The tether 160 may extend through the device catheter 118, into handle 154 and be operatively coupled with the actuator 156. The device catheter 118 and primary catheter 162 are cooperatively sized and configured so that the device catheter 118 may be advanced through the primary catheter 162 and its associated handle 164 (or, rather, through associated and co-axial lumens 168 of the handle 164 and the primary catheter 162) for deploying the medical device 110 as described hereinabove. With this arrangement, the primary catheter 162 may first be employed by advancing the primary catheter 162 through the right atrium, through the atrial septum wall via a septal puncture to enter the left atrium and navigated adjacent the LAA.

The device catheter 118 may then be advanced through the primary catheter 162 and, further, advanced beyond the distal end of the primary catheter 162 and within the LAA such as shown in FIG. 4A (only the device catheter is shown in FIG. 4A). The medical device 110 may then be deployed via the actuator 156 and anchored within the LAA with the jailing portion covering the ostium of the LAA such as is shown in FIGS. 3 and 4C. The device catheter 118 may then be withdrawn from the LAA and from the primary catheter 162.

The tissue growth member 140 (FIGS. 4D and 4E) may then be deployed within the LAA through a second, separate catheter 118a which is advanced through the primary catheter 162, the primary catheter 162 maintaining access to the LAA. In the case of a separate catheter 118a, such a catheter may be configured substantially similarly to the device catheter 118 but configured to accommodate the tissue growth member(s) 140 rather than the medical device 110.

In another embodiment, the tissue growth member 140 may be deployed directly through the primary catheter 162 by use of a pusher member. In such a case the tissue growth member 140 may be loaded into the opening 168 of the primary catheter's handle 166 and an appropriate pushing member may then be inserted through the opening 168 to advance the tissue growth member 140 through the primary catheter 162, such as described in further detail in U.S. Provisional Patent Application No. 61/143,360, filed Jan. 8, 2009, previously incorporated by reference herein in its entirety.

Figure 6:
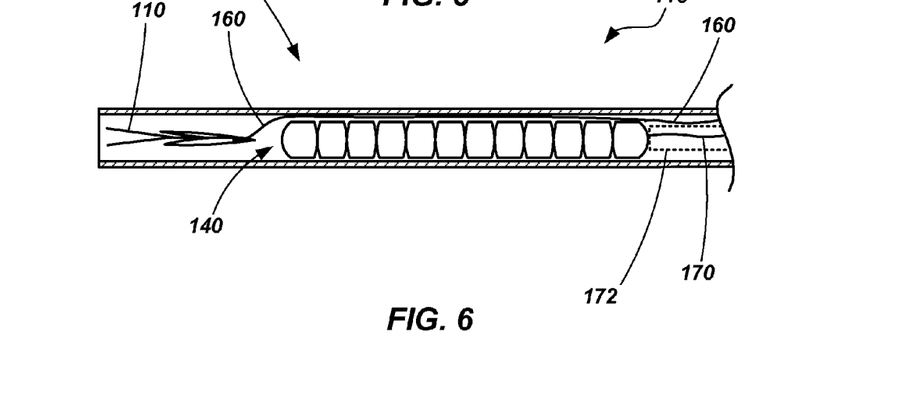
FIG. 6 is a partial cross-sectional view of the distal end of a catheter associated with a medical device system in accordance with an embodiment of the present invention.

Referring briefly to FIG. 6, in another embodiment, and as indicated above, the medical device 110 and tissue growth member 140 may be delivered to the LAA and deployed by a single catheter 118 (e.g., a device catheter 118). For example, the medical device 110 may be disposed within a distal end 166 of the catheter 118 with one or more tethers 160 coupled between the medical device 110 and an actuator (not shown in FIG. 6) such as described above with respect to FIG. 5. The tissue growth member 140 may be disposed within the catheter 118 proximally of the medical device 110. The one or more tethers 160 may pass through the catheter 118 alongside the tissue growth member 140 to the handle and actuator (not shown in FIG. 6). The medical device 110 may be deployed by, for example, moving the catheter 118 proximally a predetermined distance at one or more stages via an associated actuator. Upon deployment of the medical device 110, the one or more tethers 160 may be released or, at this stage, maintained until after deployment of the tissue growth member 140. The tissue growth member 140 may then be deployed using a second actuating mechanism (not shown) that may, for example, employ a tether 170 and a pusher member 172. The tissue growth member 140 may be deployed, for example, by positioning the catheter 118 through and opening in the medical device 110 and into the LAA so that the catheter 118 can move proximally via the second actuating mechanism and/or the pusher member can be moved distally to release the tissue growth member 140 from the catheter 118 within the LAA. The respective tethers can then be released from the medical device 110 and tissue growth member 140 and the catheter 118 may be withdrawn. Thus, various means of deploying the medical device 110 and tissue growth member 140 are contemplated.

Figure 7:
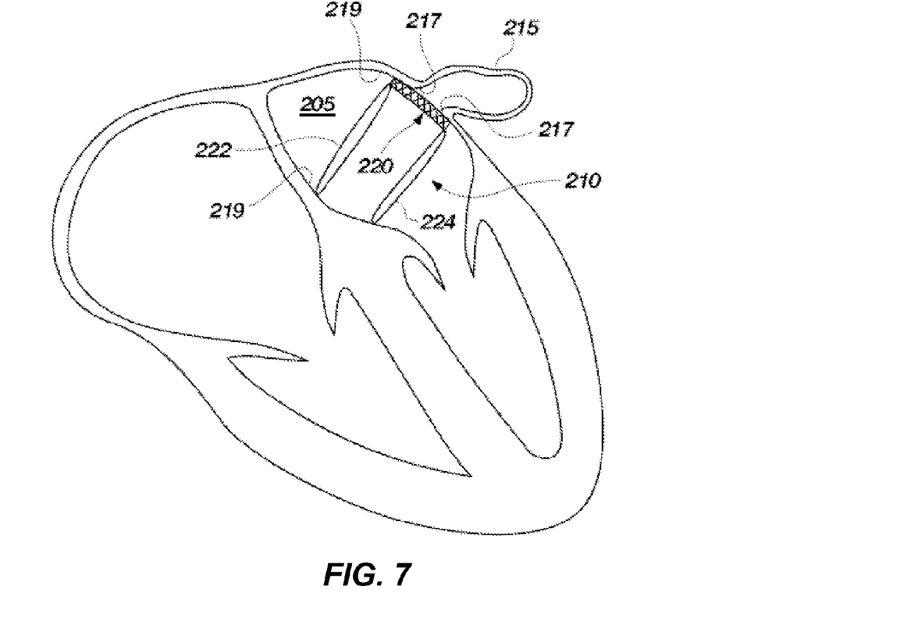
FIG. 7 is a cross-sectional view of a heart with a medical device implanted in a left atrium of the heart, depicting the medical device, in perspective view, acting as a stent in the left atrium, according to another embodiment of the present invention.
Figure 8:
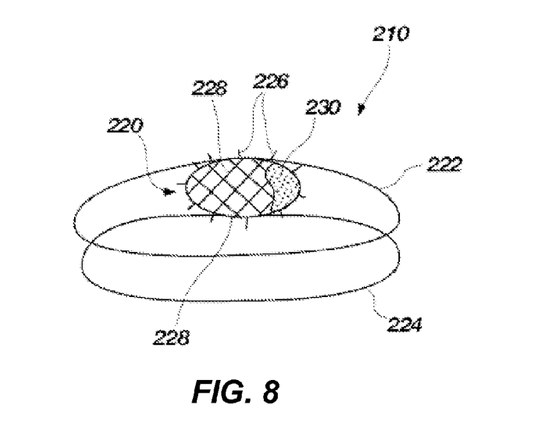
FIG. 8 is a perspective view of the medical device of FIG. 7, according to another embodiment of the present invention.

Referring now to FIGS. 7 and 8, another embodiment of a medical device 210 employed for modifying a left atrial appendage 215 is shown according to an embodiment of the present invention. In particular, in this embodiment, the medical device 210 is positioned within the atrium (e.g., the left atrium 205), and not within the atrial appendage. In other words, the medical device 210 is deployed as a stent-like structure within the left atrium 205 that provides a surface covering the ostium 217 of the left atrial appendage (LAA) 215.

In one embodiment, the medical device 210 may include a patch 220, an upper loop 222 and a lower loop 224 each extending from the patch 220. The upper loop 222 may extend from an upper portion of the patch 220 and the lower loop 224 may extend from a lower portion of the patch 220. The periphery of each of the upper loop 222 and the lower loop 224 is sized and configured to bias outwardly against the sidewall 219 of the left atrium 205 to, thereby, lodge the patch 220 within the atrium over the ostium 217 of the LAA 215. A plurality of anchors 226 may also be positioned about the patch 220. The anchors 226 may be sized and configured to engage and provide traction with the sidewall 219 of the left atrium 205 to assist maintaining the position of the patch 220 over the ostium 217.

In one embodiment, the patch 220 may include a framework 228 with multiple struts or frame segments to define a multi-cellular structure. The patch 220 may also include a tissue growth member 230. The tissue growth member 230 may include a porous member, such as a polymer based foam or a polyurethane foam. Other materials with desired porosity can also be used, such as felt, fabric, Dacron®, or Nitinol felt. In other embodiments, the tissue growth member 230 may include Nitinol braded or weaved wire. In one embodiment, the struts or frame segments may be configured as the tissue growth member, with or without the incorporation of other components (e.g., foam, braded or weaved wire). The tissue growth member is configured to induce tissue in-growth therethrough to, thereby, provide a tissue seal over the ostium of the LAA 215.

It is noted that, rather than utilizing the tissue growth member 230 described with respect to FIGS. 7 and 8 the medical device 210 may be utilized similar to that which has been described above with the patch 220 acting as a jailing mechanism to restrain or jail a separate tissue growth member (e.g., tissue growth member 140) within the LAA 215.

Figure 9:
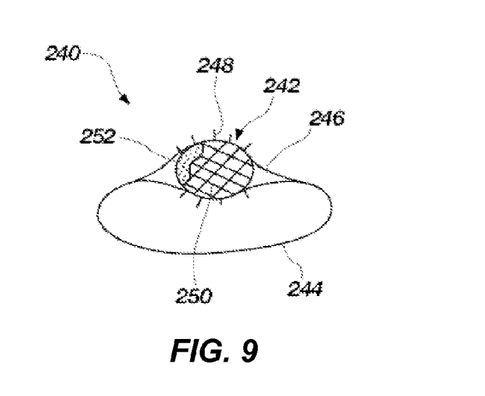
FIG. 9 is a perspective view of a medical device according to a further embodiment of the present invention.

Referring to FIG. 9, another embodiment of a medical device 240 is illustrated. The medical device 240 is configured to act like an atrial stent-like structure, similar to the embodiment described with respect to FIGS. 7 and 8. The medical device 240 may include a patch 242 with a single loop structure 244 extending from the patch. The single loop structure 244 may include a single wire or multiple wires braided or in a weaved structure. In one embodiment, the patch 242 may include extensions 246 extending from opposing sides of the patch 242 converging with each other to provide the single loop structure 244 that is sized and configured to bias outwardly against the sidewall of an atrium of the heart. In other embodiments, the single loop structure 244 may be coupled to the patch 242 by other appropriate joining means or mechanisms. Similar to the embodiment described with respect to FIGS. 7 and 8, the patch 242 may include anchors 248, a framework 250 defining a multi-cellular structure and/or a tissue growth member 252.

Figure 10:
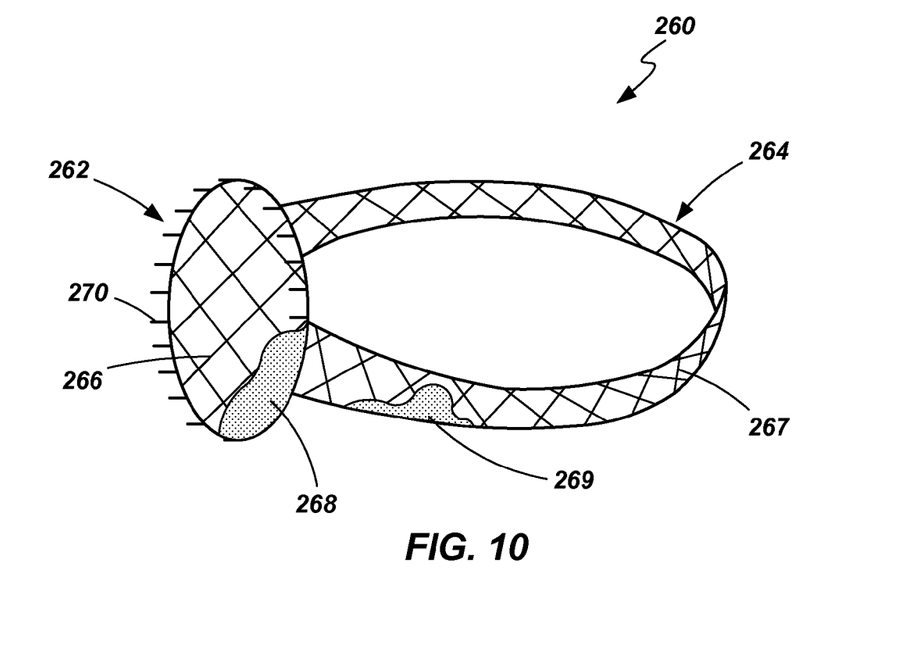
FIG. 10 is a perspective view of a medical device, depicting the medical device having a patch and framework with a multi-cellular configuration, according to another embodiment of the present invention.

FIG. 10 illustrates a further embodiment of a medical device 260 configured to act like a stent within an atrium of the heart. In this embodiment, the medical device 260 includes a patch portion 262 and a loop portion 264. The patch portion 262 and the loop portion 264 may each include a framework 266 and 267, respectively, which may be formed as a weave or of struts defining a multicellular structure. In this manner, the loop portion 264 may provide increased surface area to engage and bias against the sidewall of the left atrium when positioning and deploying the patch portion 262 over the ostium of the left atrial appendage. Further, in this embodiment, the patch portion 262, the loop portion 264, or both, may include a tissue growth member 268 and 269, respectively. The patch portion 262 may also include anchors 270 sized and configured to engage and provide traction against the sidewall of the left atrium.

Figure 11:
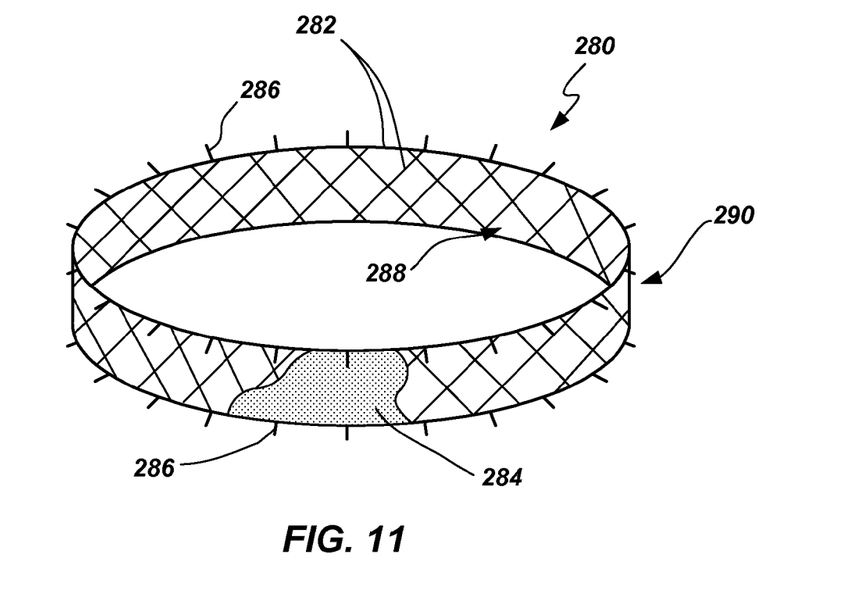
FIG. 11 is a perspective view of a medical device, depicting the medical device having a substantially continuous looped structure, according to another embodiment of the present invention.

FIG. 11 illustrates another embodiment of a medical device 280 configured to act like a stent within the left atrium. In this embodiment, the medical device 280 may include a loop-shaped framework 282 in the form of a weave or braid or any other suitable structure (e.g., a plurality of frame segments) a that defines a multi-cellular structure. Such a framework 282 may include an inner side 288 and an outer side 290. The framework 282 can include a tissue growth member 284, similar to the previous embodiments. Such tissue growth member 284 may be provided to extend substantially over the entire framework 282, over the inner side 288, the outer side 290, over both the inner side 288 and the outer side 290, or over a smaller region that is intended to cover the ostium of the left atrial appendage. Further, the medical device 280 may include anchors 286 that extend radially outward from the framework 282 to stabilize the medical device 280 within and against the sidewall of the left atrium.

As with the embodiment described with respect to FIGS. 7 and 8, the embodiments described with respect to FIGS. 9 through 11 may also be configured to act as jailing structures to retain tissue growth members (e.g., tissue growth member 140 shown in FIGS. 4D and 4E) within the LAA if desired.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes all modifications, equivalents, and alternatives falling within the spirit and scope of the invention as defined by the following appended claims.

What is claimed is:

1. A method of modifying a left atrial appendage having an ostium defining an axis, the method comprising:

positioning a jailing member over the ostium of a left atrial appendage against a left atrium side wall such that the jailing member is sized larger than the ostium and outside of the left atrial appendage, the jailing member including a hub with multiple interconnected struts extending from the hub, the multiple interconnected struts defining a multi-cellular structure movable between a constricted position and an expanded position, the struts of the jailing member in the expanded position extending to define a flat structure such that the flat structure is positioned over the ostium with an orientation substantially perpendicular to the axis of the ostium;

anchoring the jailing member against the left atrium side wall and over the ostium with an anchoring portion extending from the jailing member to engage tissue inside of the left atrial appendage;

inserting a catheter through a cell defined between the struts of the multi-cellular structure and off-set from the hub of the jailing member and into the left atrial appendage;

disposing at least one tissue growth member within the left atrial appendage via the catheter, the at least one tissue growth member being separate and discrete from the jailing member; and retaining the at least one tissue growth member within the left atrial appendage with the jailing member.

2. The method according to claim 1, further comprising providing a tensile bias between the anchoring portion and the jailing member.

3. The method according to claim 1, wherein the step of positioning a jailing member over the ostium of a left atrial appendage includes delivering the jailing member to the left atrial appendage with a first catheter, and wherein the step of inserting a catheter through a cell defined between the struts of the multi-cellular structure and off-set from the hub of the jailing member and the step of disposing at least one tissue growth member within the left atrial appendage includes inserting a second catheter through the opening within the jailing member and delivering the at least one tissue growth member with the second catheter.

4. The method according to claim 3, further comprising advancing the first catheter through a primary catheter to access the left atrial appendage, withdrawing the first catheter from the primary catheter subsequent delivering the jailing member to the left atrial appendage, and advancing the second catheter through the primary catheter subsequent withdrawing the first catheter.

5. The method according to claim 1, wherein the step of disposing at least one tissue growth member within the left atrial appendage further includes disposing a plurality of tissue growth elements within the left atrial appendage.

6. The method according to claim 5, further comprising connecting the plurality of tissue growth elements with a tether.

7. The method according to claim 1, wherein the step of anchoring comprises anchoring with the anchor portion extending from a proximate center of the jailing member.

8. The method according to claim 1, wherein the step of anchoring comprises anchoring the jailing member with the anchoring portion having nubs to atraumatically engage tissue in the left atrial appendage.

9. The method according to claim 1, wherein the step of anchoring comprises anchoring the jailing member with the anchoring portion extending from an intermediate anchoring portion oriented substantially perpendicular relative to the flat structure of the jailing member and the anchoring portion including multiple legs extending from the intermediate anchoring portion to engage tissue in the left atrial appendage.

* * * * *